United States Patent [19]

Johnston

[11] 3,931,201

[45] Jan. 6, 1976

[54] SUBSTITUTED PYRIDINYLOXY(THIO)PHENYL -ACETAMIDES, -UREAS AND UREA DERIVATIVES

[75] Inventor: Howard Johnston, Walnut Creek, Calif.

[73] Assignee: The Dow Chemical Company, Midland, Mich.

[22] Filed: Jan. 22, 1974

[21] Appl. No.: 435,615

[52] U.S. Cl. ........ 260/294.8 H; 71/94; 260/293.69; 260/294.9; 260/295 E; 260/295.5 D
[51] Int. Cl.² ........................................ C07D 213/02
[58] Field of Search ... 260/295 E, 295.5 D, 294.8 H

[56] References Cited
UNITED STATES PATENTS

| | | |
|---|---|---|
| 3,060,235 | 10/1962 | Martin et al. ........................ 260/553 |
| 3,412,098 | 11/1968 | Winkelmann et al. ............ 260/294.8 |
| 3,429,689 | 2/1969 | Duerr et al. ............................ 71/94 |
| 3,530,138 | 9/1970 | Undheim et al. ................. 260/294.8 |
| 3,576,616 | 4/1971 | Nowotny ................................ 71/94 |
| 3,637,720 | 1/1972 | Nishiyama et al. ............. 260/297 R |

*Primary Examiner*—Norman A. Drezin
*Attorney, Agent, or Firm*—S. Preston Jones

[57] ABSTRACT

Disclosed are novel substituted pyridinyloxy(thio)phenyl-acetamides, -ureas and urea derivatives, N-oxide derivatives thereof, and certain novel intermediates therefore. The compounds of the instant invention are useful as herbicides and can be formulated to provide herbicidal compositions.

14 Claims, No Drawings

SUBSTITUTED PYRIDINYLOXY(THIO)PHENYL -ACETAMIDES, -UREAS AND UREA DERIVATIVES

SUMMARY OF THE INVENTION

The present invention is directed to substituted pyridinyloxy(thio)phenyl -acetamides, -ureas and urea derivatives corresponding to the formula:

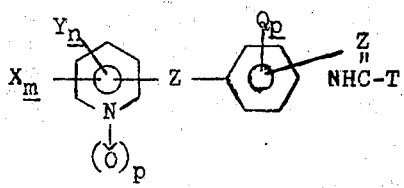

wherein:

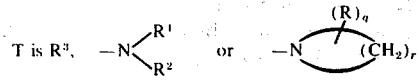

$r$ represents an integer of 4 or 5;
$q$ represents an integer of 0 to 2, inclusive;
each $p$ independently represents an integer of 0 or 1;
each X independently represents bromo, chloro, iodo or fluoro;
$m$ represents an integer of 0 to 4, inclusive;
each Y independently represents cyano, nitro, $ZR^3$, $—C(X')_3$ or

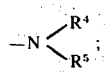

$n$ represents an integer of 0 to 2, inclusive;
each Z independently represents oxygen or sulfur;
Q represents methyl, ethyl, halo, nitro, cyano or trifluoromethyl;
each X' independently represents hydrogen or halo;
each R independently represents hydrogen or an alkyl group of from about 1 to about 3 carbon atoms;
$R^1$ represents hydrogen, an alkyl group of from about 1 to about 4 carbon atoms or an alkoxy group of from about 1 to about 4 carbon atoms;
$R^2$ represents an alkyl group of from about 1 to about 3 carbon atoms or

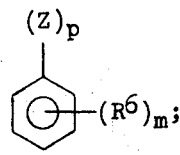

$R^3$ represents an alkyl group of from about 1 to about 3 carbon atoms;
$R^4$ and $R^5$ each independently represents hydrogen or an alkyl group of from about 1 to about 4 carbon atoms; and
each $R^6$ represents halo or an alkyl group of from about 1 to about 3 carbon atoms.

For the sake of brevity and simplicity, the term "active ingredient" is used hereinafter in this specification to broadly describe the compounds of the present invention. In the reaction sequences set forth below, all substituents, unless otherwise expressly indicated, are the same as set forth above.

The active ingredients of the present invention are normally crystalline solids and are soluble in the usual organic solvents, as well as having some solubility in water. The active ingredients are useful as plant growth regulants, and especially as herbicides when applied either as a pre-emergence or post-emergence treatment and may be formulated with the usual herbicide carriers for use in controlling unwanted plants.

DETAILED DESCRIPTION

The active ingredients of the present invention are useful as herbicides, particularly as post-emergent herbicides. Several of the active ingredients of the present invention have been found suitable for controlling unwanted plants among crops such as, for example, soybeans, corn and rice, without injuring the crops. As used in the present specification and claims, the term "herbicide" means an active ingredient which, when used in a growth controlling amount, controls or modifies the growth of plants. By a "growth controlling amount" is meant an amount of compound which causes a modifying effect upon the growth of plants. Such modifying effects include all deviations from natural development, for example, killing, retardation, defoliation, desiccation, regulation, stunting, tillering, and the like. By "plants" it is meant germinant seeds, emerging seedlings, and established vegetation, including the roots and above-ground portions.

The term "alkyl" is used herein and in the appended claims to designate a straight or branched chain alkyl radical containing from 1 to about 4 carbon atoms, such as, for example, methyl, ethyl, propyl, isopropyl, butyl, isobutyl and tert-butyl. The term "alkoxy" as employed designates a straight or a branched-chain radical containing from 1 to about 4 carbon atoms, such as, for example, methoxy, ethoxy, propoxy, isopropoxy, butoxy, isobutoxy and tertbutoxy.

The terms "halo" and "halogen" are employed herein to represent chlorine, fluorine and bromine.

Preferred compounds of the present invention are those compounds wherein $n$ is 0 and $m$ is at least 1. In a further preferred embodiment, $m$ is 0 and $n$ is at least 1. Another preferred class of compounds are those wherein the sum of $m + n$ is one and X or Y is ring substituted in the 6-ring position of the pyridine moiety. In another embodiment, those compounds wherein the sum of $m + n$ is at least two are preferred. In an additional preferred embodiment, T is $R^3$. Another class of preferred compounds includes those wherein T is

A further class of preferred compounds includes those wherein T is

and $R^1$ and $R^2$ each represent alkyl. Still another preferred class of compounds includes those wherein T is

$R^1$ is alkoxy and $R^2$ is alkyl. An additional preferred class is directed to compounds wherein T is

m is 1, n is 0 and X is in the 6-ring position of the pyridine moiety. A further preferred class of compounds are those wherein T is

n is 1, m is 0 and Y is in the 6-ring position of the pyridine moiety. In still another preferred embodiment, T is

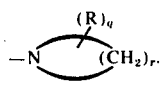

The active ingredients of the present invention are prepared by a variety of methods. The active ingredients wherein T is $R^3$ (i.e., alkyl of from 1 to about 3 carbon atoms), which are hereinafter referred to as "acetamide" compounds, can be prepared by reacting an appropriately substituted halopyridine with a selected sodium acetamidophenate reactant in the presence of an inert solvent under reflux conditions. Such reaction can be represented schematically as follows:

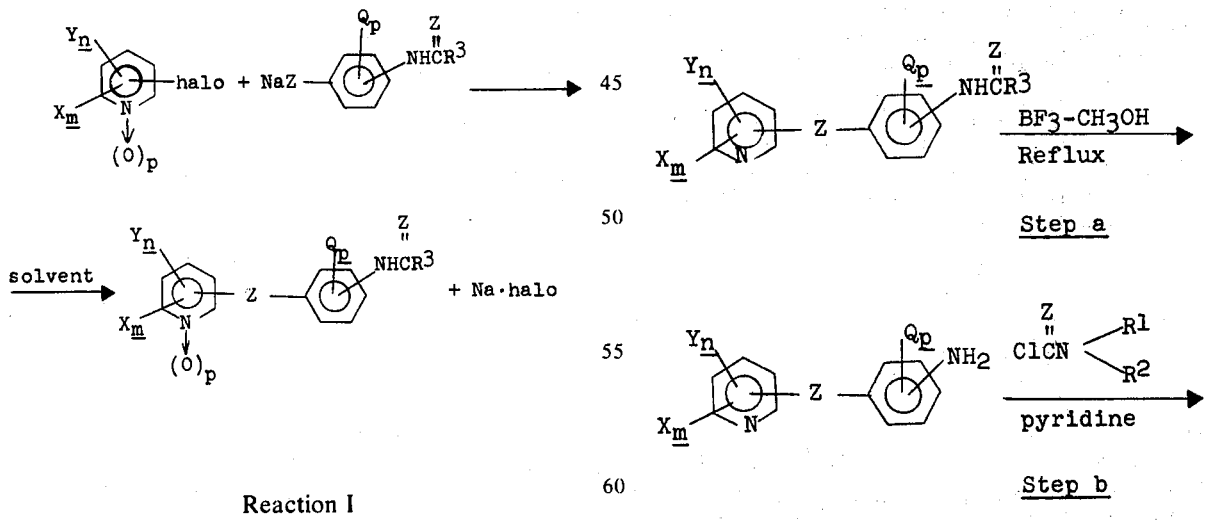

Reaction I

Reaction I proceeds readily under ambient atmospheric pressure at temperatures of from about 90° to about 150°C. A solution of the sodium acetamidophenate reactant in methanol is added portionwise, ordinarily dropwise, to a solution of the substituted halopyridine reactant in an inert solvent such as, for example, dimethylsulfoxide, hexamethylphosphoramide, dimethylformamide, and the like. Stoichiometric proportions of the reactants are usually employed.

The sodium acetamidophenate solution, which can be prepared by rapidly adding stoichiometric proportions of acetamidophenol to a solution of sodium metal in dry methanol, is usually added dropwise to a well-stirred solution of halopyridine over a peroid of from about 30 to about 90 minutes. The reactants are usually mixed at ambient temperatures and heated to the refluxing temperature of the mixture, which is thereafter maintained for a period of time sufficient to substantially complete the reaction. Depending upon the rate of reaction, the reaction mixture may be refluxed for a period of time from about one to about eight hours. Following the completion of the reaction, the reaction mixture is allowed to cool, mixed with ice water and the resulting precipitate filtered off, washed again with water and dried. The so-dried reaction product can be employed as such in further operations or further purified by recrystallization from a solvent or solvent mixture, such as, for example, benzene/hexane, benzene/methylene chloride and the like.

The active ingredients of the present invention wherein T is $-NR^1R^2$ (wherein $R^1$ and $R^2$ are hydrogen or alkyl and all other substitutents are as previously defined, conveniently hereinafter referred to as "phenyl urea" compounds), are, with the exception of the N-oxide derivatives thereof, readily prepared by converting the acetamide products of Reaction I to a corresponding amine intermediate. Such amine intermediates are novel and hence are considered an integral part of the present invention. The novel amine intermediates, which can be obtained by refluxing the acetamide products of reaction I with borontrifluoride in the presence of methanol, are reacted with an appropriately substituted (thio)-carbamoyl halide reactant, such as a carbamoyl chloride, in the presence of pyridine to form the corresponding phenyl urea compounds. The reaction can be schematically represented as follows:

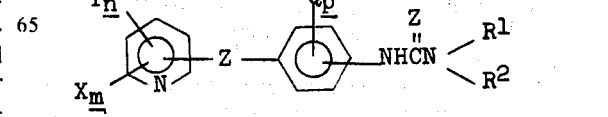

Reaction II

The reaction to convert the acetamide products to the corresponding amine intermediates (step a, Reaction II) proceeds readily under ambient atmospheric pressure and at the reflux temperature of the reaction mixture. In such operations, the acetamide product is mixed with a solution of borontrifluoride in methanol and the resulting reaction mixture is heated to the refluxing temperature of the mixture for a period of from about 2 to about 3 hours. An excess of borontrifluoride is usually employed. The methanol solvent is then usually distilled off and the concentrated reaction mixture is cooled, poured into cold water and treated with concentrated aqueous ammonia until the solution is basic. The resulting product precipitate is recovered by filtration, washed and recrystallized if desired from a solvent such as, for example, benzene, methylene chloride and the like. The aqueous filtrate remaining after recovery of the product precipitate can also be extracted with such solvents to recover additional quantities of the desired amine product.

The amine intermediates prepared above are, in step b of Reaction II, reacted with an appropriately substituted carbamoyl halide reactant in the presence of dry pyridine to obtain the desired phenyl urea compounds of the instant invention. The reaction proceeds readily under ambient temperature and pressure conditions. Generally, stoichiometric amounts of the reactants are employed. In carrying out the reaction, the total quantity of the carbamoyl halide reactant is usually added all at once to a solution of the amine reactant in pyridine and the resulting reaction mixture allowed to stand at ambient temperatures for a period of from about 15 to about 30 hours. The reaction mixture is then poured into cold water and allowed to stand for a short period of time. The resulting product precipitate is recovered by filtration and mixed with a solvent, such as one of those hereinbefore mentioned. The resulting solvent-product solution is dried, treated with norite and concentrated by evaporation to crystallize out the desired phenyl urea product.

The N-oxide derivatives of the above "phenylurea" compounds are usually prepared by other methods in view of the high reactivity of the N-oxide ($N \rightarrow O$) group with certain reagents, such as the borontrifluoride reagent employed in step (a) of Reaction II. In such method, the salt of a selected substituted amino(thio)phenol reactant of the formula:

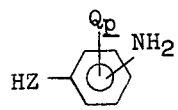

is reacted with the N-oxide derivative of a selected substituted halopyridine reactant to obtain the N-oxide form of the desired pyridinyloxy(thio)benzenamine intermediate. The latter reaction is carried out employing procedures analogous to those employed in Reaction I above. The benzenamine intermediate can be reacted with a carbamoyl halide reactant as in step (b) of Reaction II to obtain the desired N-oxide derivatives of the pyridinyloxy(thio)phenylurea compounds of the present invention.

In other procedures, the above amino(thio)phenol reactant can be reacted with a selected carbamoyl halide reactant, as in step (b) of Reaction II, to obtain a corresponding hydroxy- or mercapto- phenylurea reactant. The thus-obtained phenylurea reactant can be reacted with an N-oxide halopyridine reactant in the presence of a base, such as, for example, sodium metal in methanol, sodium hydroxide or the like, and a solvent carrier, such as previously mentioned herein, at temperatures ordinarily ranging from about 20° to about 80°C. or higher for a period generally from about 1 to about 6 or more hours. The desired pyridinyloxy(thio)phenylurea-1-oxide derivative is recovered in a manner similar to recovery procedures previously set forth.

The N-oxide derivatives of the halopyridine reactants employed above as starting materials are prepared according to conventional oxidative procedures. In typical known types of operations, the selected halopyridine reactant is treated with anhydrous trifluoroacetic acid and excess 90% hydrogen peroxide under reflux conditions to obtain the desired N-oxide derivative.

The novel amine intermediates employed in Reaction II can also be employed in alternative procedures for the preparation of the acetamide compounds of the instant invention. In such operations, a selected substituted amine intermediate is reacted with a selected substituted acid halide, such as, for example, acetyl chloride, propionyl chloride, butyryl chloride and the like. The reaction is carried out by mixing the reactants, ordinarily in stoichiometric proportions, in the presence of an inert solvent, such as, for example, pyridine, and maintaining the resulting reaction mixture at ambient temperatures for a period of from about 16 to about 24 hours. The reaction mixture is then mixed with cold water and the resulting product precipitate recovered and purified in procedures analogous to those set forth for Reaction I.

The novel amine intermediates described above in relation to Reaction II, with the exception of the N-oxide derivatives thereof, can also be prepared in alternative procedures whereby a selected salt of a nitro(thio)phenol is reacted with an appropriate substituted halopyridine compound to form the corresponding substituted nitrophenoxy- or nitrophenylthio- pyridine compound, which is then reduced to the corresponding aminophenoxy or aminothiophenyl- pyridine compound with a reducing agent, such as iron powder. This reaction can be represented as follows:

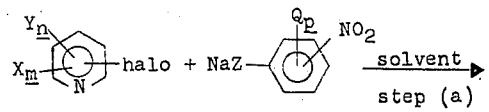

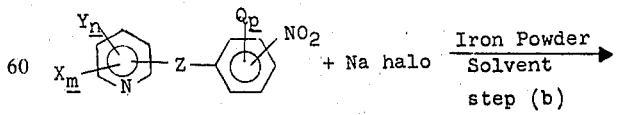

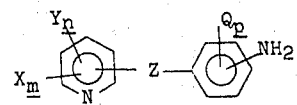

Reaction III

The reaction in step (a) of Reaction III proceeds readily under ambient atmospheric pressure at reaction temperatures of from about 100° to about 160°C. for a period of from about 3 to about 5 hours. In such operations, the salt of the substituted nitrophenol or nitrothiophenol is mixed with the selected halopyridine reactant in the presence of an inert solvent, such as previously mentioned with respect to Reaction I, and the resulting reaction mixture heated at a temperature within the above indicated ranges. Following the substantial completion of the reaction, the reaction mixture is cooled and mixed with cold water. The resulting product precipitate is recovered by filtration and recrystallized according to conventional techniques from a solvent such as, for example, benzene, methylene chloride and the like.

The product thus obtained from step (a) of Reaction III is mixed, in the presence of an aqueous alcohol solution, with a reducing agent, such as, for example, iron powder. The resulting reaction mixture is heated to the reflux temperature thereof with vigorous stirring and an alcohol solution of concentrated hydrochloric acid is added thereto, portionwise, over a 10 to 30 minute period. The reaction mixture is then heated at the reflux temperature for a period of from about 2 to about 4 hours and then filtered while hot. The solid product thus obtained is washed with an aqueous alkanol solution, such as 50-95% ethanol, and the filtrate portions combined and extracted with a solvent such as benzene, methylene chloride or the like. The extract is then dried, treated with activated charcoal, such as Norite, filtered and evaporated to dryness to obtain the desired aminophenoxy- or aminothiophenyl- pyridine product as a crystalline solid or oily liquid.

The N-oxide derivatives of the benzenamine intermediates can also be prepared by first reducing the nitro(-thio)phenol reactant to the corresponding amino(thio)phenol reactant with a reducing agent as in step (b) of Reaction III and then reacting the salt of such amino(thio)phenol reactant with the N-oxide derivative of the halopyridine reactant employing procedures analogous to those set forth in Reaction I. Such alternative procedures are employed in this instance in view of the high reactivity of the N-oxide group with a reducing agent.

In still other procedures, the foregoing amino(thio)-phenol reactant can be reacted with phosgene or thiophosgene, as in step (a) of Reaction IV (hereinafter set forth), to obtain a corresponding phenyliso(thio)cyanate reactant which can be reacted (a) with a selected substituted pyrrolidine or piperidine reactant, as in the following Reaction IV, to obtain a corresponding hydroxy- or mercaptophenyl (pyrrolidine- or piperidine-)carboxamide reactant or (b) with a selected hydroxyl- or mercapto amine reactant, as in the following Reaction V, to obtain a corresponding hydroxy- or mercapto- phenylurea reactant. The latter carboxamide and phenylurea reactants can be reacted with an N-oxide halopyridine reactant in the presence of a base, such as, for example, sodium hydroxide or sodium metal in methanol, and a solvent carrier, such as previously mentioned herein, at temperatures ordinarily ranging from about 20° to about 80°C. or higher for a period generally from about 1 to about 6 or more hours. The desired pyridinyloxy(thio)phenyl ((pyrrolidine- or piperidine-)carboxamide) or -urea products are recovered in a manner similar to the recovery procedures set forth hereinabove.

The pyrrolidine- and piperidine- carboxamide derivatives of the present invention, i.e., wherein T is

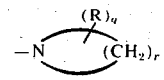

are prepared by reacting the amine intermediates of the present invention (prepared in step (a) of Reaction II or step (b) of Reaction III) with phosgene or thiophosgene in the presence of toluene to form a corresponding novel pyridinyloxy- or pyridinylthio- phenyl iso- or isothio- cyanate intermediate, hereinafter referred to as "isocyanate" intermediates, which is then reacted with a selected pyrrolidine or piperidine reactant to obtain the desired product. The essential steps of the reaction sequence can be schematically illustrated as follows:

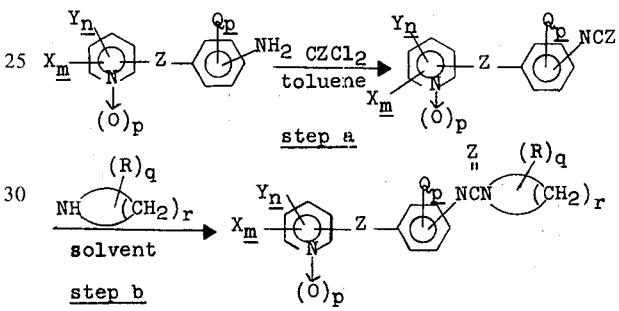

Reaction IV

The isocyanate intermediates are readily prepared according to step (a) above by first preparing a solution of phosgene or thiophosgene in a solvent such as, for example, water, toluene or the like, and then rapidly adding, with stirring, a solution of the amine starting material in toluene. The amine addition is regulated so as to maintain the temperature of the mixture at about 5°C. or less, with additional quantities of solvent being added if necessary. Following the completion of the amine addition, the reaction mixture is agitated and heated gradually until a temperature of from about 75° to about 95°C. is reached. The solvent carrier is then removed from the reaction mixture by evaporation under reduced pressure and the remaining residue taken up in hexane which is then cooled to crystallize the desired product. An excess of phosgene or thiophosgene, in a ratio of from about 3 to about 4 moles thereof per mole of amine reactant, is preferably employed in the reaction. During the reaction, excess phosgene can be removed by purging the reaction mixture with an inert gas, such as nitrogen.

In step (b) of Reaction IV, the isocyanate intermediate is reacted with the selected pyrrolidine or piperidine reactant under reaction conditions generally the same as for the hereinbefore described procedures in step (b) of Reaction II. Stoichiometric quantities of the reactants are usually employed.

The isocyanate intermediates prepared in step (a) of Reaction IV are employed in the preparation of compounds of the instant invention wherein T is

and R¹ is alkoxy and R² is alkyl. Other phenyl urea compounds of the present invention can also be prepared from the isocyanate intermediates. In such operations, the isocyanate intermediates are reacted with an appropriately substituted hydroxyl amine salt reactant in the presence of a base and an inert solvent, such as, for example, triethylamine and pyridine according to the following illustrative reaction sequence:

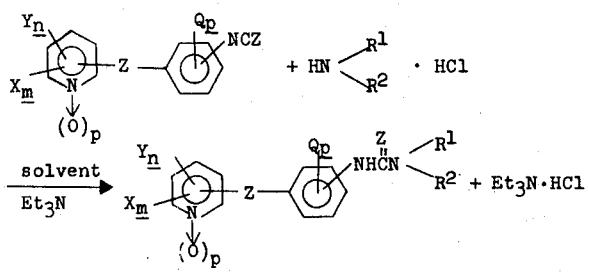

Reaction V

The reaction is conducted under ambient atmospheric pressure at temperatures of from about 50° to about 100°C. Preferably, an actuating agent is employed to increase to the reaction rate. Representative actuating agents that can be employed include, for example, tertiary amines such as triethylamine and the like. The reactants are usually employed in stoichiometric proportions while an excess of the actuating agent is employed.

In carrying out the reaction, the isocyanate and substituted hydroxylamine reactants are contacted in the presence of a dry inert solvent containing the actuating agent. Representative solvents include, for example, pyridine, toluene or the like. The resulting reaction mixture is heated with stirring at a temperature within the above described range for a period of from about one-half to about 2 or more hours. The reaction mixture is then stirred at ambient temperatures for a period of from about 1 to about 12 hours and then cooled and mixed with cold water. The resulting product precipitate is recovered and purified in typical procedures previously set forth.

The following examples illustrate the present invention and the manner by which it can be practiced but, as such, should not be construed as limitations upon the overall scope of the same.

EXAMPLE 1

N-(4-((6-bromo-2-pyridinyl)oxy)phenyl)acetamide

A solution of sodium methylate was prepared by adding sodium metal (1.6 grams; 0.07 mole) to 50 milliliters (ml) of dry methanol. 4-Acetamidophenol (10.6 grams; 0.07 mole) was added to the solution in a rapid manner and the resulting solution of sodium 4-acetamidophenate was then added portionwise, over a period of about one hour, to an agitated solution of 2,6-dibromopyridine (6.6 grams; 0.07 mole) in 70 ml. of dimethylsulfoxide. The reaction mixture was distilled during the addition of the phenate solution to remove methanol and maintain the temperature of the reaction mixture in the range of from about 126° to about 132°C. Following the completion of the addition of the phenate solution, distillation of the reaction mixture was stopped and the reaction mixture was allowed to stand at ambient temperatures for a period of about 16 hours. The reaction mixture was then refluxed for about 2¼ hours at a temperature of about 127°C. and then cooled and poured into ice water, stirred and the resulting solid precipitate representing the desired N-(4-((6-bromo-2-pyridinyl)oxy)phenyl)acetamide compound removed by filtration, washed and dried. The recovered product was found to have carbon, hydrogen, nitrogen and bromine contents of 50.4, 3.7, 9.08 and 27.56 percent, respectively, as compared with the theoretical contents of 50.8; 3.6; 9.1 and 26.0 percent, respectively, calculated for the named structure.

EXAMPLE 2

N-(4-((6-chloro-2-pyridinyl)thio)phenyl)-acetamide

4-Acetamidothiophenol (16.8 grams; 0.1 mole) was mixed with a solution of sodium methylate (prepared by mixing sodium metal (2.3 grams; 0.1 mole) in 90 ml. of methanol) and the resulting sodium 4-acetamidothiophenol solution added over a period of about one hour to a well-stirred solution of 2,6-dichloropyridine (14.8 grams; 0.1 mole) in 100 ml. of dimethylsulfoxide. The reaction mixture was distilled during the addition and the reaction temperature maintained at about 100°C. for this period and for a period of about two hours thereafter. The reaction mixture was then poured into 350 ml. of water and the resulting product precipitate recovered by filtration, washed several times and taken up in 300 ml. of hot benzene and dried and treated with Norite. About 350 ml. of hexane was added to precipitate the product from the benzene solvent which was recovered by filtration. As a result of such operations, the desired N-(4-((6-chloro-2-pyridinyl)thio)-phenyl)acetamide compound was recovered as a crystalline solid which was found to have carbon, hydrogen, nitrogen, chlorine and sulfur contents of 56.2, 4.3, 9.9, 11.4 and 11.63 percent, respectively, as compared with the theoretical contents of 56.0, 3.96, 10.05, 12.7 and 11.45, respectively, calculated for the named structure.

EXAMPLE 3

N-(3-chloro-4-((6-chloro-2-pyridinyl)oxy)phenyl)propionamide 4-((6-Chloro-2-pyridinyl)oxy)-3-chlorobenzeneamine (7.1 grams; .028 mole) and propionyl chloride (2.6 grams; .028 mole) were contacted in the presence of 40 ml. of dry pyridine and the resulting reaction mixture allowed to stand at ambient temperatures for a period of about 18 hours. The reaction mixture was then poured into 250 ml. of cold water and allowed to stand for about 15 minutes. The resulting product precipitate was recovered by filtration and taken up in boiling benzene and the resulting solution dried, treated with Norite and filtered. Hexane was then added to the filtrate which was then cooled to precipitate the desired N-(3-chloro-4-((6-chloro-2-pyridinyl)oxy)phenyl)propionamide compound as a white crystalline solid having a melting point of 166°–168°C. The product was found to have carbon, hydrogen, nitrogen and chlorine contents of 55.0, 3.9, 9.0 and 22.5, respectively, as compared with the theoretical contents of 54.0, 3.9, 9.0 and 22.8, respectively, calculated for the named structure.

EXAMPLE 4

N'-(4-((6-chloro-2-pyridinyl)thio)phenyl)-N,N-dimethyl urea

N-(4-((6-chloro-2-pyridinyl)thio)phenyl)acetamide (18.15 grams; 0.065 mole) from Example 2 above was mixed with 220 ml. of a solution of borontrifluoride ($BF_3$) in methanol (10 grams of $BF_3$ in 100 ml. of methanol) and the resulting reaction mixture was heated at the reflux temperature of the reaction mixture for a period of two hours. The reaction mixture was then cooled to about 0°C. and 105 ml. of concentrated aqueous ammonia added gradually, while maintaining the reaction mixture at from about 0° to about 5°C., until the reaction mixture was basic. Methanol and ammonia were then distilled off under reduced pressure and the residue containing the precipitated product was recovered by filtration and recrystallized from hexane. As a result of these operations, the desired 4-((6-chloro-2-pyridinyl)thio)benzenamine intermediate product was recovered as a crystalline solid which was found to have carbon, hydrogen, nitrogen, chlorine and sulfur contents of 55.8, 3.9, 12.20, 15.1 and 13.3 percent, respectively, as compared with the theoretical contents of 55.7, 3.84, 11.72, 15.0 and 13.55 percent, respectively, calculated for the named structure.

The benzenamine intermediate (6.85 grams; 0.029 mole) was mixed with 20 ml. of dry pyridine and dimethyl carbamoyl chloride (3.1 grams; 0.029 mole) was added thereto at ambient temperatures. The resulting reaction mixture was allowed to stand at ambient temperatures for a period of about 15 hours, following which it was poured into 200 ml. of cold water. After standing for a few minutes, the resulting product precipitate was recovered by filtration and recrystallized from toluene. The recovered N'-(4-((6-chloro-2-pyridinyl)thio)phenyl)-N,N-dimethyl urea compound had a melting point of 187°–188°C. and was found to have carbon, hydrogen, nitrogen, chlorine and sulfur contents of 54.8, 4.9, 13.2, 11.42 and 10.4 percent, respectively, as compared with the theoretical contents of 54.7, 4.58, 13.65, 11.55 and 10.4 percent, respectively, calculated for the named structure.

EXAMPLE 5

4-((6-fluoro-2-pyridinyl)oxy)benzenamine

A mixture of 2,6-difluoropyridine (20.2 grams; 0.175 mole) and dry sodium p-nitrophenate (28.2 grams; 0.175 mole) in 130 ml. of dry dimethylsulfoxide was heated at a temperature of about 110°C. for a period of about 4 hours. Following the completion of the reaction period, the reaction mixture was cooled, poured into 325 ml. of cold water and allowed to stand for a few minutes. The resulting crystallized product was recovered by filtration and recrystallized from a 50:50 benzene-hexane mixture. The desired 2-fluoro-6(4-nitrophenoxy)pyridine intermediate (19.1 grams; 0.018 mole) which was obtained as a crystalline solid melting at 104°–105°C. and iron powder (15 grams; 0.268 mole) were mixed in 115 ml. of 50% aqueous ethanol and the resulting reaction mixture heated at the reflux temperature thereof. Concentrated hydrochloric acid (5.5 ml. in 20 ml. of 50% ethanol) was added thereto, portionwise, with vigorous stirring over a period of about 15 minutes. The reaction mixture was then refluxed for a period of 3 hours, cooled, poured into water and neutralized with an aqueous sodium hydroxide solution. The resulting solid cake was recovered by filtration and extracted with two 300 ml. portions of benzene. The extracts were combined and treated with activated charcoal, filtered, and the filtrate evaporated to obtain the desired 4-((6-fluoro-2-pyridinyl)oxy)benzenamine product as a white crystalline solid having carbon, hydrogen and nitrogen contents of 65.2, 4.6 and 13.9 percent, respectively, as compared with contents of 64.8, 4.4 and 13.7 percent, respectively, calculated for the named structure.

EXAMPLE 6

4-((6-chloro-2-pyridinyl)oxy)phenyl isocyanate

A stream of phosgene was passed into 120 ml. of dry toluene maintained at a temperature of about 0° to about 5°C. until a weight of 13.4 grams (0.135 mole) had been absorbed. 4-((6-Chloro-2-pyridinyl)oxy)benzenamine (10.0 grams; 0.045 mole) in 100 ml. of dry toluene was then added to the stirred phosgene solution over a period of about 15 minutes while maintaining the reaction temperature within a range of about 2° to about 5°C. Following the completion of the addition, the reaction mixture was stirred for about 20 minutes and the reaction temperature then gradually raised as excess phosgene was purged with a stream of nitrogen. When a reaction temperature of about 85°C. was attained, the reaction mixture became clear. The toluene solvent was then substantially removed under reduced pressure and hexane added to the residue to give the desired 4-((6-chloro-2-pyridinyl)oxy)phenyl isocyanate product as a white crystalline product having a melting point of 96°–97° C.

EXAMPLE 7

4-((6-chloro-2-pyridinyl)oxy)phenyl isothiocyanate

Thiophosgene (10.5 grams; 0.091 mole) was added to an agitated solution of water (170 ml.) and dimethoxyethane (25 ml.) 4-((6-Chloro-2-pyridinyl)oxy)benzenamine (20 grams; 0.0906 mole) was added in small portions (the dimethoxyethane aids in suspending the amine in the aqueous thiophosgene solution) to the stirred thiophosgene solution over a 20 minute period. The reactive temperature during the addition was 25°–30°C. Following the addition of the amine reactant, the reaction mixture was filtered to recover the product precipitate which formed during the reaction. The precipitate was then dissolved in boiling hexane and the resulting solution dried and cooled to give the desired 4-((6-chloro-2-pyridinyl)oxy)phenyl isothiocyanate product as a light yellow crystalline solid having a melting point of 59°–62°C. The product was found to have carbon, hydrogen, nitrogen, chlorine and sulfur contents of 55.5, 2.3, 10.9, 13.36 and 12.34 percent, respectively, as compared with the theoretical contents of 54.82, 2.69, 10.66, 13.5 and 12.2 percent, respectively, calculated for the named structure.

EXAMPLE 8

N-(4-((6-chloro-2-pyridinyl)oxy)phenyl)-2,5-dimethyl-1-pyrrolidine carboxamide 2,5-Dimethylpyrrolidine (2.5 grams; 0.0284 mole) was added at ambient temperature to a solution of 4-((6-chloro-2-pyridinyl)oxy)phenyl isothiocyanate, prepared as in Example 7 (7.0 grams; 0.0284 moles) in 25 ml. of dry pyridine. The resulting reaction mixture was allowed to stand at ambient temperatures for a period of about 16 hours and then poured into 300 ml. of cold water. The resulting product precipitate was recovered by filtration, washed with water and taken up in boiling benzene. Hexane was then added to the solution and the solution cooled to precipitate the desired N-(4-((6-chloro-2-pyridinyl)oxy)phenyl)-2,5-dimethyl-1-pyrrolidine carboxamide compound as a crystalline solid having a carbon, hydrogen, nitrogen and chlorine content of 62.2, 5.7, 11.9 and 10.2 percent, respectively, as compared with contents of 62.5, 5.82, 12.5 and 10.25 percent, respectively, calculated for the named structure.

EXAMPLE 9

N'-(4-((6-chloro-2-pyridinyl)oxy)phenyl)-N-methoxy-N-methyl urea 4-((6-chloro-2-pyridinyl)oxy)phenyl isocyanate (4.0 grams; 0.0162 mole), prepared according to Example 6, and N-methyl-O-methyl hydroxylamine hydrochloride (1.6 grams; 0.0162 mole) were added to 25 ml. of dry pyridine containing 5.0 grams of triethylamine actuating agent. The resulting reaction mixture was heated intermittently to about 60°C. over a period of about one-half hour and then poured into cold water. The resulting precipitate, representing the desired N'-(4-((6-chloro-2-pyridinyl)oxy)phenyl)-N-methoxy-N-methyl urea compound, was recovered by filtration and recrystallized from benzene. The crystalline product thus obtained was found to have a melting point of 96°–97°C., and carbon, hydrogen, nitrogen and chlorine contents of 54.7, 4.8, 13.7 and 11.64 percent, respectively, as compared to the theoretical contents of 54.6, 4.58, 13.65 and 11.55 percent, respectively, calculated for the named structure.

EXAMPLE 10

N-((4-chlorophenyl)thio)-N'-(4-((6-chloro-2-pyridinyl)oxy)phenyl)-N-methylurea 4-Chlorobenzenesulfenyl chloride (8.68 grams; 0.0496 mole) was added over a period of about 3 minutes to a solution of N'-(4-((6-chloro-2-pyridinyl)oxy)-phenyl-N-methylurea (8.3 grams; 0.03 mole) in 50 ml. of dry pyridine. The resulting reaction mixture was stirred at a temperature of about 30°C. for a period of about one and one-half hours and then poured into 250 ml. of cold water. The resulting sticky product precipitate was dissolved in hot hexane, reprecipitated therefrom upon standing and the light-yellow, slightly sticky product obtained triturated with a small amount of cold acetonitrile. Filtration of the mixture gave the desired N-((4-chlorophenyl)thio)-N'-(4-((6-chloro-2-pyridinyl)oxy)phenyl)-N-methylurea compound as a white crystalline solid melting at 106°–109°C. The product was found to have carbon, hydrogen, nitrogen, chlorine and sulfur contents of 54.2, 3.5, 9.86, 17.0 and 7.46 percent, respectively, as compared with contents of 54.3, 3.6, 10.0, 16.87 and 7.6 percent, respectively, as calculated for the named structure.

EXAMPLE 11

N'-(4-((6-chloro-2-pyridinyl)oxy)phenyl)-N,N-dimethylurea-1-oxide

Dry powdered sodium hydroxide (2.44 grams; 0.061 mole) was dissolved in 110 ml. of warm dimethylsulfoxide and N'-(4-hydroxyphenyl)-N,N-dimethyl urea (11.0 grams; 0.061 mole) and 2,6-dichloropyridine-N-oxide added thereto. The reaction mixture was stirred at a temperature of about 60°C. for a period of five and one-half hours. After this period, about three-fourths of the solvent carrier was removed by vacuum distillation and the residual oil thus obtained poured into ice water. The aqueous mixture was extracted with three 250 ml. portions of warm methylene chloride and the extracts combined. Evaporation of the solvent from the extract left a brown, syrupy residue which was washed with cold water and then with dry benzene to give the desired N'-(4-((6-chloro-2-pyridinyl)oxy)phenyl)-N,N-dimethyl urea-1-oxide compound as a crystalline solid melting at 190°–191°C. and having carbon, hydrogen, nitrogen and chlorine contents of 53.83, 4.63, 13.25 and 12.78 percent, respectively, as compared with contents of 54.64, 4.58, 13.65 and 11.52 percent, respectively, calculated for the named structure.

Other urea compounds and derivatives are similarly prepared from selected substituted amine or isocyanate intermediates in accordance with the procedures of Examples 4, 8, 9, 10 and 11 and the foregoing teachings of the specification. Such other compounds include, inter alia, the following:

N'-(4-((3,5,6-trichloro-2-pyridinyl)oxy)phenyl)-N,N-dimethyl urea (184°–185°C.);

N'-(4-((6-fluoro-2-pyridinyl)oxy)phenyl)-N,N-dimethyl urea (149°–153°C.);

N'-(4-((6-chloro-2-pyridinyl)oxy)phenyl)-N,N-dimethyl urea (132°C.);

N'-(4-((6-(trifluoromethyl)-2-pyridinyl)oxy)-phenyl)-N,N-dimethyl urea (121°–123°C.);

N'-((3-(6-fluoro-2-pyridinyl)oxy)phenyl)-N,N-dimethyl urea (131°–132°C.);

N'-(4-((6-methoxy-2-pyridinyl)oxy)phenyl)-N,N-dimethyl urea (132°–140°C.);

N'-(3-((6-(trifluoromethyl)-2pyridinyl)oxy)phenyl)-N,N-dimethyl urea (119°–120°C.);

N'-((3-(6-chloro-2-pyridinyl)oxy)phenyl)-N,N-dimethyl urea (121°–123°C.);

N'-((4-(5-cyano-2-pyridinyl)oxy)phenyl)-N,N-dimethyl urea (143°C.);

N'-(4-((3,5-dichloro-6-fluoro-2-pyridinyl)oxy)-phenyl)-N,N-dimethyl urea (170°–173°C.);

N'-(4-((4,6-bis(trifluoromethyl)-2-pyridinyl)oxy)-phenyl)-N,N-dimethyl urea (133°–135°C.);

N'-((3-(5-chloro-2-pyridinyl)oxy)phenyl)-N,N-dimethyl urea (98°–99°C.);

N'-(4-((6-fluoro-2-pyridinyl)oxy)phenyl)-N,N-dimethylthio urea (155°–160°C.);

N'-((4-(6-fluoro-2-pyridinyl)oxy)phenyl)-N-methylurea (161°–163°C.);

N'-((4-(6-cyano-2-pyridinyl)oxy)phenyl)-N,N-dimethylurea (163°–165°C.);

N'-(4-((6-bromo-2-pyridinyl)oxy)phenyl)-N,N-dimethylurea (144.5°–146.5°C.);

N'-(4-((5-chloro-2-pyridinyl)oxy)phenyl)-N,N-dimethylurea (130°–131°C.);

N,N-dimethyl-N'-(4-(2-pyridinyloxy)phenyl)urea (165°–167°C.);

N'-(4-((6-chloro-4-(trifluoromethyl)2-pyridinyl)oxy)phenyl)-N,N-dimethylurea (149.5°–150.5°C.);

N,N-dimethyl-N'-(4-((5-nitro-2-pyridinyl)oxy)phenyl)-urea;

N,N-dimethyl-N'-(4-((6-(methylthio)-2-pyridinyl)oxy)phenyl)urea (126°–129°C.);

N'-(4-((6-chloro-2-pyridinyl)oxy)phenyl)-N,N-diethylurea (162°–163°C.);

N'-(4-((3-chloro-2-pyridinyl)oxy)phenyl)-N,N-dimethylurea (163°–165°C.);

N'-(4-((3,5-dichloro-2-pyridinyl)oxy)phenyl)-N,N-dimethylurea (160.3°–161.3°C.);

N,N-dimethyl-N'-(4-((6-methyl-2-pyridinyl)oxy)phenyl)urea (128°–131°C.);

N,N-dimethyl-N'-(4-((3,6-dichloro-2-pyridinyl)oxy)phenyl)urea (147°–150°C.);

N'-(4-((6-chloro-5-cyano-2-pyridinyl)oxy)phenyl)-N,N-dimethylurea;

N'-(4-((6-chloro-2-pyridinyl)thio)phenyl)-N,N-dimethylurea (187°–188°C.);

N'-(4-((5-chloro-6-cyano-2-pyridinyl)oxy)phenyl)-N,N-dimethylurea;

N'(4-((6-(chlorodifluoromethyl)-2-pyridinyl)oxy)phenyl)-N,N-dimethylurea (138°–139°C.);

N'-(4((6-bromo-2-pyridinyl)oxy)phenyl)-N-methoxy-N-methylurea (95°–100°C.);

N'-(4-((6-fluoro-2-pyridinyl)oxy)phenyl)-N-methoxy-N-methylurea (111°–113°C.);

N'-(4-((4-chloro-6-trifluoromethyl)-2-pyridinyl)oxy)phenyl)-N,N-dimethylurea (179°–184°C.);

N'-(4((6-chloro-4-(trifluoromethyl)-2-pyridinyl)oxy)phenyl)-N-methoxy-N-methylurea (137°–140°C.);

N-methoxy-N-methyl-N'-(4-(((6-trifluoromethyl)-2-pyridinyl)oxy)phenyl)urea (115°–117°C.);

N'-(4-((3-cyano-2-pyridinyl)oxy)phenyl)-N,N-dimethylurea (179°–180°C.);

N,N-dimethyl-N'-(4-((6-(propylthio)-2-pyridinyl)oxy)phenyl)urea (129.7°–132.2°C);

N'-(4-((6-chloro-2-pyridinyl)oxy)-3-(trifluoromethyl)phenyl)-N,N-dimethylurea (142°–143°C.);

N,N-dimethyl-N'-(4-((6-(trifluoromethyl)-2-pyridinyl)thio)phenyl)urea (195°–197°C.);

N,N-dimethyl-N'-(4-((6-propoxy)-2-pyridinyl)oxy)phenyl)urea (118°–122°C.);

N'-(4-((6bromo-2-pyridinyl)thio)phenyl)-N,N-dimethylurea (157.5°–161.5°C.);

N'-(4-((6-chloro-2-pyridinyl)thio)phenyl)-N-methoxy-N-methylurea (140°–142°C.);

N'-(4-((6-fluoro-2-pyridinyl)thio)phenyl)-N,N-dimethylurea (154°–156°C.);

N-butyl-N'-(4-((6-chloro-2-pyridinyl)oxy)phenyl)-N-methylurea (99°–101°C.);

N-(4-((6-chloro-2-pyridinyl)oxy)phenyl)-2,5-dimethyl-1-pyrrolidinecarboxamide (127°–130°C.);

N,N-dimethyl-N'-(4-(4-methyl-2-pyridinyl)oxy)phenyl)urea (158°–160°C.);

N'-(4-((4,6-dimethyl-2-pyridinyl)oxy)phenyl)-N,N-dimethylurea;

N'-(4-((5-chloro-6-cyano-2-pyridinyl)oxy)phenyl)-N-methoxy-N-methylurea (141°–143°C.);

N'-(4-((5-chloro-6-cyano-2-pyridinyl)thio)phenyl)-N,N-dimethylurea (195°–198°C.);

N'-(4-((6-chloro-4-(chlorodifluoromethyl)-2-pyridinyl)oxy)phenyl)-N,N-dimethylurea (165°–166°C.);

N'-(4-((6-chloro-2-pyridinyl)oxy)phenyl)-N,N-dimethylthiourea (135°–138°C.);

N'-(4-((6-iodo-2-pyridinyl)oxy)phenyl)-N,N-dimethylurea (109°–112°C.);

N'-(4-((6-chloro-2-pyridinyl)oxy)phenyl)-N-methoxy-N-methylthiourea (125°–127°C.);

N-butyl-N'-(4-((6-chloro-2-pyridinyl)oxy)phenyl)-N-methylthiourea (77°–79°C.);

N'-(4-((6-bromo-2-pyridinyl)oxy)phenyl)-N,N-dimethylthiourea (141.5°–142.5°C.);

N'-(4-((6-chloro-2-pyridinyl)oxy)phenyl)-N,N-dimethylurea-1-oxide (M.P. 190°–191°C.);

N-butoxy-N'-(4-((3,4,5,6-tetrabromo-2-pyridinyl)thio)phenyl)-N-methylurea;

N-methoxy-N-propyl-N'-(3-((4-pyridinyl)oxy)phenyl)-thiourea;

N-((3,4,5-trichlorophenyl)oxy)-N'-(3-((4-chloro-6-amino-2-pyridinyl)oxy)phenyl)-N-methylurea;

N'-(3-((2,6-dicyano-4-pyridinyl)oxy)-4-ethylphenyl)-N-methoxy-N-methylurea;

N'-(4-((6-(trifluoromethyl)-3-pyridinyl)thio)-3-cyanophenyl)-N,N-ethylurea;

N-butyl-N'-(4-((5-(dichloromethyl)-3-pyridinyl)oxy)-2-nitrophenyl)-N-propylurea;

N'-(5-((2-bromo-6-methylamino-4-pyridinyl)thio)-3-bromophenyl)-N-butyl-N-methylthiourea;

N-butoxy-N'-(3-((5-(dichloromethyl)-3-pyridinyl)oxy)-4-cyanophenyl)-N-propylurea;

N'-(4-((4-methyl-3,5,6-trichloro-2-pyridinyl)thio)-3-methylphenyl)-N,N-dimethylurea;

N'-(4-((4,5-dimethyl-3,6-dichloro-2-pyridinyl)oxy)-3-fluorophenyl)-N-methyl-N-methoxy thiourea;

N-(4-((4,6-dinitro-2-pyridinyl)oxy)phenyl)-3-propyl-1-piperidinecarboxamide;

N-(4-((5-chloro-2,6-dimethoxy-4-pyridinyl)oxy)-3-chlorophenyl)-2,6-dimethyl-1-piperidinethiocarboxamide;

N'-(5-((6-bromo-4-n-butylamino-2-pyridinyl)thio)-3-(trifluoromethyl)phenyl)-N-ethoxy-N-methylthiourea;

N'-(3-((6-chloro-4-di-n-butylamino-5-methyl-2-pyridinyl)oxy)phenyl)-N,N-dimethylurea;

N-(4-((5,6-dichloro-3-cyano-4-propoxy-2-pyridinyl)thio)-2-chlorophenyl)-1-pyrrolidinecarboxamide;

N'-(4-((2,6-diamino-3,5-dichloro-4-pyridinyl)oxy)phenyl)-N,N-dimethylurea;

N'-(5-((6-chloro-4,5-dinitro-2-pyridinyl)thio)-3-methylphenyl)-N,N-di-n-propylurea;

N-((3,5-di-i-propylphenyl)oxy)-N'-(4((2,6-bis(trifluoromethyl)-4-pyridinyl)oxy)-N-methylthiourea;

N'-(4-((3,5,6-trichloro-4-(difluoromethyl)-2-pyridinyl)oxy)phenyl)-N,N-dimethylurea;

N'-(3-((5-bromo-3,6-dichloro-4-(trifluoromethyl)-2-pyridinyl)thio-2-methylphenyl)-N-methylurea;

N'-(4-((2,6-di-(dimethylamino)-4-pyridinyl)thio)phenyl)-N-methoxy-N-methylthiourea;

N-(4-((3,4,5,6-tetrachloro-2-pyridinyl)oxy)phenyl)-1-pyrrolidine carboxamide and N'-(4-((4-cyano-6-(trifluoromethyl)-2-pyridinyl)thio)phenyl)-N,N-dimethylthiourea.

The novel amine and isocyanate intermediates which are employed, inter alia, to prepare the foregoing are readily apparent in view of the specific enumerated compounds. Such amine intermediates are of the formula represented in Reaction Sequences III and IV of the specification and are prepared in accordance with the teachings of the specification and the foregoing Examples 4, 5 and 6. The nomenclature for such compounds is as set forth in such examples. The novel isocyanate intermediates employed to prepare, inter alia, the above-enumerated compounds are likewise readily apparent in view of the above-enumerated compounds as well as the amine intermediates used therein and from which the isocyanate intermediates are themselves prepared. Such isocyanate intermediates correspond to the general formula represented in reaction sequences IV and V set forth hereinbefore. Such novel intermediates are prepared according to the teachings of the specification and representative examples 6 and 7, which also set forth the nomenclature of such compounds. The novel acetamide intermediates, which are useful as intermediates in preparing the corresponding novel amine intermediates and which also have utility as herbicides, include those which correspondingly are employed to prepare the readily apparent amine intermediates, in turn used in preparing the compounds enumerated above. Such acetamide compounds correspond to the formula set forth in reaction sequence I and are prepared according to the teachings of the specification and Examples 1–3, wherein the nomenclature for such compounds is set forth.

The compounds of the present invention have been found to be suitable for use in methods for the pre- and post-emergent control of weeds or other unwanted vegetation. Certain of the active ingredients of the present invention have been found to be active against undesired vegetation in the presence of desired crop plants while producing only a negligible effect on the crop plants. For all such uses, unmodified active ingredients of the present invention can be employed. However, the present invention embraces the use of a herbicidally effective amount of the active ingredients in composition form with a material known in the art as an adjuvant or carrier in solid or liquid form. Thus, for example, an active ingredient can be dispersed on a finely divided solid and employed therein as a dust. Also, the active ingredients, as liquid concentrates or solid compositions comprising one or more of the active ingredients, can be dispersed in water, typically with the aid of a wetting agent, and the resulting aqueous dispersion employed as a spray. In other procedures, the active ingredient can be employed as a constituent of organic liquid compositions, oil-in-water and water-in-oil emulsions, or water dispersions, with or without the addition of wetting, dispersing, or emulsifying agents.

Suitable adjuvants of the foregoing type are well known to those skilled in the art. The methods of applying the solid or liquid herbicidal formulations similarly are well known to the skilled artisan.

As organic solvents used as extending agents there can be employed hydrocarbons, e.g., benzene, toluene, xylene, kerosene, diesel fuel, fuel oil, and petroleum naphtha, ketones such as acetone, methyl ethyl ketone and cyclohexanone, chlorinated hydrocarbons such as carbon tetrachloride, chloroform, trichloroethylene, and perchloroethylene, esters such as ethyl acetate, amyl acetate and butyl acetate, ethers, e.g., ethylene glycol monomethyl ether and diethylene glycol monomethyl ether, alcohols, e.g., methanol, ethanol, isopropanol, amyl alcohol, ethylene glycol, propylene glycol, butyl Carbitol acetate and glycerine. Mixtures of water and organic solvents, either as solutions or emulsions, can be employed.

The active ingredients can also be applied as aerosols, e.g., by dispersing them in air by means of a compressed gas such as dichlorodifluoromethane or trichlorofluoromethane and other Freons and Genetrons, for example.

The active ingredients of the present invention can also be applied with adjuvants or carriers such as talc, pyrophyllite, synthetic fine silica, attapulgus clay, keiselguhr, chalk, diatomaceous earth, lime, calcium carbonate, bentonite, fuller's earth, cottonseed hulls, wheat flour, soybean flour, pumice, tripoli, wood flour, walnut shell flour, redwood flour and lignin.

As stated, it is frequently desirable to incorporate a surface active agent in the compositions of the present invention. Such surface active or wetting agents are advantageously employed in both the solid and liquid compositions. The surface active agent can be anionic, cationic or nonionic in character.

Typical classes of surface active agents include alkyl sulfonate salts, alkylaryl sulfonate salts, alkylaryl polyether alcohols, fatty acid esters of polyhydric alcohols and the alkylene oxide addition products of such esters, and addition products of long chain mercaptans and alkylene oxides. Typical examples of such surface active agents include the sodium alkylbenzene sulfonates having 10 to 18 carbon atoms in the alkyl group, alkylphenol ethylene oxide condensation products, e.g., p-isooctylphenol condensed with 10 ethylene oxide units, soaps, e.g., sodium stearate and potassium oleate, sodium salt of propylnapthalene sulfonic acid, di(2-ethylhexyl)ester of sodium sulfosuccinic acid, sodium lauryl sulfate, sodium decane sulfonate, sodium salt of the sulfonated monoglyceride of coconut fatty acids, sorbitan sesquioleate, lauryl trimethyl ammonium chloride, octadecyl trimethyl ammonium chloride, polyethylene glycol lauryl ether, polyethylene glycol esters of fatty acids and rosin acids, e.g. Ethofat 7 and 13, sodium N-methyl-N-oleyl taurate, Turkey Red Oil, sodium dibutyl naphthalene sulfonate, sodium lignin sulfonate, polyethylene glycol stearate, sodium dodecylbenzene sulfonate, tertiary dodecyl polyethylene glycol thioether (nonionic 218), long chain ethylene oxide-propylene oxide condensation products, e.g., Pluronic 61 (molecular weight 1000), polyethylene glycol ester of tall oil acids, sodium octyl phenoxyethoxyethyl sulfate, tris-(polyoxyethylene)sorbitan monostearate (Tween 60), and sodium dihexyl sulfosuccinate.

The concentration of the active ingredients in liquid compositions generally is from about 0.001 to about 95 percent by weight or more. Concentrations of from about 0.001 to about 50 weight percent are often employed. In dusts or dry formulations, the concentration of the active ingredient can be from about 0.001 to about 95 weight percent or more; concentrations of from about 0.001 to about 50 weight percent are often conveniently employed. In compositions to be employed as concentrates, the active ingredient can be present in a concentration of from about 5 to about 98 weight percent. The active ingredient compositions can also contain other compatible additaments, for example, phytotoxicants, plant growth regulants, pesticides and the like and can be formulated with solid particulate fertilizer carriers such as ammonium nitrate, urea and the like.

The present compositions can be applied by the use of power-dusters, boom and hand sprayers, spray-dusters, by addition to irrigation water, and by other conventional means. The compositions can also be applied from airplanes as a dust or a spray because they are effective in very low dosages.

The exact dosage to be applied is dependent not only upon the specific active ingredient being employed, but also upon the particular plant species to be modified and the stage of growth thereof, as well as the part of the plant to be contacted with the toxic active ingredient. Thus, it is to be understood that all of the active ingredients of the invention and compositions containing the same may not be equally effective at similar concentrations or against the same plant species. In non-selective pre-emergence and foliage treatments the compositions of this invention are usually applied at an approximate rate of from about 1 to about 25 lbs. per acre, but lower or higher rates may be appropriate in some cases. In selective post-emergence operations to foliage, a dosage of from about 0.16 to about 5.0 pounds per acre is usually employed. In some instances, lower dosages may be utilized while higher dosages may be necessary in other instances. In view of the foregoing and following disclosures, one skilled in the art can readily determine the optimum rate to be applied in any particular case.

So as to illustrate the general and selective phytotoxic properties of the active ingredients of the present invention, a group of controlled greenhouse experiments is described below. In such operations, the various seeds and plants employed are represented by letters as follows:

A. German Millet
B. Foxtail
C. Barnyard Grass
D. Crabgrass
E. Johnson Grass
F. Wild oat
G. Pigweed
H. Bindweed
I. Velvet leaf
J. Morning Glory
K. Wild Mustard
L. Cocklebur M. Rice
N. Wheat
O. Corn
P. Soybean
Q. Cotton
R. Sorghum
S. Coffee weed
T. Prickly Sida
U. Ground Cherry
V. Lambsquarter
W. Jimson Weed In pre-emergence operations, seeds of selected species are planted in seedbeds and, while exposed, sprayed with a given volume of a solution containing a predetermined amount of the candidate active ingredient to provide the dosage rate desired. Such compositions are prepared by mixing the selected active ingredient and an emulsifier or dispersant with water. The seeds are then covered with a layer of soil and maintained under conditions conducive to growth. A portion of the planted seedbeds are left untreated to provide controls for comparative purposes. All seedbeds are watered from below as needed. About 14 days after seeding and treating, the effect of each of the test ingredients on the seeds is evaluated by a comparison with the control seedbeds.

In post-emergence operations, various species of plants are seeded in beds of good agricultural soil. After the plants have emerged and grown to a height of from about 2 to 6 inches, certain of the plants are sprayed to run-off with a given volume of a composition prepared as set forth above. Other plants are left untreated to provide comparative controls. All plants are maintained as above for a period of about 14 days and then evaluated to determine the effect of each test ingredient.

In representative general pre-emergence operations, each of the N'-(4-(((6-trifluoromethyl)-2-pyridyl)oxy)phenyl)-N,N-dimethyl urea (Compound 1);N'-(4-((6-chloro-2-pyridinyl)oxy)phenyl)-N-methoxy-N-methyl urea (Compound 2); N'-(4-((6-bromo-2-pyridinyl)oxy)phenyl)-N-methoxy-N-methyl urea (Compound 3); N-methoxy-N-methyl-N'-((((6-trifluoromethyl)-2-pyridinyl)oxy)phenyl)urea (Compound 4); N'-(4-((6-(chlorodifluoromethyl)-2-pyridinyl)oxy)phenyl)-N,N-dimethyl urea (Compound 5) and N'-(4-((6-fluoro-2-pyridinyl)oxy)phenyl)-N-methoxy-N-methyl urea (Compound 6) compounds was found to give substantial (at least 70%) to complete (100%) inhibition of the growth of plant species A, C, D, E, F, G, H, I, J, and K at a dosage rate of approximately 5.0 pounds per acre. In similar general operations, each of the N'-(4-((4,6-dimethyl-2-pyridinyl)oxy)phenyl)-N,N-dimethyl urea (Compound 7) and N'-(4-((5-chloro-6-cyano-2-pyridinyl)oxy)phenyl)-N-methoxy-N-methyl urea (Compound 8) compounds was found to give substantial to complete inhibition of growth of species A, E, G and K at a dosage rate of 5.0 pounds per acre.

In representative selective pre-emergence operations, it was found that N'-(4-((6-chloro-2-pyridinyl)thio)phenyl)-N,N-dimethyl urea (Compound 9), Compound 1, Compound 2, Compound 3, Compound 4 and Compound 5 each gives from 90 to 100% control of the growth of pigweed seeds with little or no inhibition on the growth of desirable crop seeds such as soybeans (P), corn (O) and cotton (Q) at a dosage rate of about 0.6 pounds per acre. In other operations, it was found that N'-(4-((5-chloro-6-cyano-2-pyridinyl)oxy)phenyl)-N,N-dimethyl urea (Compound 10) gave complete control of the growth of species (D) and (G) with no inhibition on the growth of desirable crop species (O), (Q) and (R) at an application rate of about 1.25 pounds per acre.

In additional pre-emergence operations, each of the N'-((4-(6-bromo-2-pyridinyl)oxy)phenyl)-N,N-dimethyl urea (Compound 11), N'-(4((6-chloro-4-(trifluoromethyl)-2-pyridinyl)oxy)phenyl)-N,N-dimethyl urea (Compound 12), N,N-dimethyl-N'-(4-((6-methyl-2-pyridinyl)oxy)phenyl)urea (Compound 13), N'-(4-((6-chloro-4-(trifluoromethyl)-2-pyridinyl)oxy)phenyl)-N-methoxy-N-methyl urea (Compound 14), N-butyl-N'-(4-((6-chloro-2-pyridinyl)oxy)phenyl)-N-methyl urea (Compound 15), N,N-dimethyl-N'-(4-((4-methyl-2-pyridinyl)oxy)phenyl)urea (Compound 16), N-((4-chlorophenyl)thio)-N'-(4-((6-chloro-2-pyridinyl)oxy)phenyl)-N-methyl urea (Compound 17) and Compound 7 was found to give complete control of, inter alia, species (D), (G) and (I) at dosage rates of about 10 pounds per acre.

In representative general post-emergence operations, each of N'-(4-((3,5,6-trichloro-2-pyridyl)oxy)phenyl)-N,N-dimethyl urea (Compound 18) and N'-(4-((3-cyano-2-pyridinyl)oxy)phenyl)-N,N-dimethyl urea (Compound 19) was found to give complete control of (G) at a dosage rate of about 10 pounds per acre. N'-(4-((6-Chloro-2-pyridinyl)oxy)phenyl)-N,N-dimethyl urea (Compound 20) was similarly found to be effective in the post-emergence control of (I) while N'-(4-((6-bromo-2-pyridinyl)thio)phenyl)-N,N-dimethyl urea (Compound 21) was found to give substantial control of (A), (C), (D), (G), (H), and (I), at dosage rates of about 10 pounds per acre, respectively.

In additional operations, each of Compounds 9, 13, 14, 15 and 16 and N,N-dimethyl-N'-(4-(2-pyridinyloxy)phenyl)urea (Compound 22), N'-(4-((3,5-dichloro- 6-fluoro-2-pyridinyl)oxy)phenyl)-N,N-dimethyl urea (Compound 23), N'-(4-((4-chloro-6-(trifluoromethyl)-2-pyridinyl)oxy)phenyl)-N,N-dimethyl urea (Compound 24), N,N'dimethyl-N'-(4-((6-(propylthio)-2-pyridinyl)oxy)phenyl)urea (Compound 25), N'-(4-((6-chloro-2-pyridyl)oxy)-3-(trifluoromethyl)-phenyl)-N,N-dimethyl urea (Compound 26), N,N-dimethyl-N'-(4-((6-(trifluoromethyl)-2-pyridinyl)thio)phenyl)urea (Compound 27), N,N-dimethyl-N'-(4-((6-propoxy)-2-pyridyl)oxy)phenyl)urea (Compound 28), N'-(4-((6-chloro-2-pyridinyl)thio)phenyl)-N-methoxy-N-methyl urea (Compound 29), N'-(4-((6-fluoro-2-pyridinyl)thio)phenyl)-N,N-dimethyl urea (Compound 30), N-(4-((6-chloro-2-pyridinyl)oxy)phenyl)-2,5-dimethyl-1-pyrrolidinecarboxamide (Compound 31), N'-(4-((6-chloro-4-(chlorodifluoromethyl)-2-pyridinyl)oxy)phenyl)-N,N-dimethyl urea (Compound 32) and N'-(4-((6-chloro-2-pyridinyl)oxy)phenyl)-N,N-dimethylthiourea (Compound 33) were found to be effective as post-emergence herbicides at a dosage rate of about 10.0 pounds per acre. The post-emergence activity is set forth in the following Table I.

Table I

| Cmpd. No. | Plant Type/Percent Control | | | | | | | |
|---|---|---|---|---|---|---|---|---|
| | A | C | D | E | G | H | I | J |
| 9 | 100 | 100 | 100 | 25 | 0 | 0 | 100 | 100 |
| 13 | 100 | 100 | 100 | 35 | 100 | 100 | 100 | 100 |
| 14 | 100 | 100 | 100 | 0 | 100 | 100 | 100 | 100 |
| 15 | 100 | 100 | 100 | 100 | 100 | 100 | 100 | 100 |
| 16 | 100 | 100 | 100 | — | 100 | 100 | 100 | 100 |
| 22 | 100 | 100 | 100 | 100 | 100 | — | 100 | 100 |
| 23 | 100 | 35 | 100 | 20 | 20 | 40 | 30 | 100 |
| 24 | 100 | 100 | 100 | 100 | 100 | 100 | 100 | 100 |
| 25 | 0 | 100 | 40 | 0 | 100 | 100 | 100 | 35 |
| 26 | 100 | 100 | 100 | 100 | 100 | 100 | 100 | 100 |
| 27 | 100 | 100 | 100 | 100 | 100 | 100 | 100 | 100 |
| 28 | 100 | 100 | 100 | 100 | 40 | 50 | 100 | 100 |
| 29 | 100 | 100 | 30 | 35 | 100 | 100 | 100 | 100 |
| 30 | 100 | 100 | 100 | 50 | 100 | 100 | 100 | 100 |
| 31 | 100 | 100 | 100 | 25 | — | 100 | 100 | 100 |
| 32 | 100 | 100 | 100 | 100 | 100 | 100 | 100 | 100 |
| 33 | 100 | 100 | 100 | 100 | 100 | 100 | 100 | 100 |

Additional post-emergence operations employing compounds (1), (2), (4), (5), (10), (11), (12), N,N-dimethyl-N'-(4-((3,6-dichloro-2-pyridinyl)oxy)phenyl)urea (Compound 34), N'-(4-((6-chloro-2-pyridinyl)oxy)phenyl)-N,N-dimethyl urea (Compound 35), N'-(4-((5-chloro-6-cyano-2-pyridinyl)thio)phenyl)-N,N-dimethyl urea (Compound 36), N'-(4-((6-fluoro-2-pyridyl)oxy)phenyl)-N,N-dimethyl urea (Compound 37), N'-((3-(6-fluoro-2-pyridinyl)oxy)phenyl)-N,N-dimethyl urea (Compound 38), N'-(3-((6-(trifluoromethyl)-2-pyridinyl)oxy)phenyl)-N,N-dimethyl urea (Compound 39), N'-((3-(6-chloro-2-pyridinyl)oxy)phenyl)-N,N-dimethyl urea (Compound 40), N'-(4-((4,6-bis(trifluoromethyl)-2-pyridinyl)oxy)phenyl)-N,N-dimethyl urea (Compound 41), N,N-dimethyl-N'-(4-((6-(methylthio)-2-pyridinyl)oxy)phenyl)urea (Compound 42), N,N-dimethyl-N'-(4-((5-nitro-2-pyridinyl)oxy)phenyl)urea (Compound 43), N'-((4-(6-cyano-2-pyridinyl)oxy)phenyl)-N,N-dimethyl urea (Compound 44), N'-(4-((5-chloro-2-pyridinyl)oxy)phenyl)-N,N-dimethyl urea (Compound 45), N'-((4-(6-fluoro-2-pyridinyl)oxy)phenyl)-N-methylurea (Compound 46), N'-(4-((6-fluoro-2-pyridinyl)oxy)phenyl)-N,N-dimethylthiourea (Compound 47), N'-(4-((6-methoxy-2-pyridinyl)oxy)phenyl)-N,N-dimethyl urea (Compound 48), N'-(4-((3-chloro-2-pyridinyl)oxy)phenyl)-N,N-dimethyl urea (Compound 49), N'-(4-((3,5-dichloro-2-pyridinyl)oxy)phenyl)-N,N-dimethyl urea (Compound 50), N'-((3-(5-chloro-2-pyridinyl)oxy)phenyl)-N,N-dimethyl urea (Compound 51), N'-(4-((6-iodo-2-pyridinyl)oxy)phenyl)-N,N-dimethyl urea (Compound 52), N'-(4-((6-chloro-2-pyridinyl)oxy)phenyl)-N-methoxy-N-methoxy-N-methylthiourea (Compound 53), N-butyl-N'-(4((6-chloro-2-pyridinyl)oxy)phenyl)-N-methylthiourea (Compound 54), and N'-(4-(( 6-bromo-2-pyridinyl)oxy)phenyl)-N,N-dimethylthiourea (Compound 55) against various plant species is reported in the following Table II. The data also indicate the selective activity of several compounds in the presence of desired crop plants at lower dosage rates.

TABLE II

| Cmpd. No. | Dosage lbs/Acre | Plant Species/% Control | | | | | | | | | | | | | | | | | |
|---|---|---|---|---|---|---|---|---|---|---|---|---|---|---|---|---|---|---|---|
| | | Weeds | | | | | | | | | | | | | | | Crops | | | |
| | | A | B | C | D | E | G | H | I | J | K | L | S | T | U | V | W | N | O | P |
| 1a. | 5.0 | — | 100 | 100 | 100 | 100 | 100 | — | — | 100 | 100 | 100 | — | — | — | — | 90 | 100 | 100 | |
| b. | .63 | 100 | 100 | 100 | 100 | 90 | 100 | 100 | 100 | 100 | 100 | 100 | 100 | 100 | 100 | 100 | 100 | 0 | 40 | 100 |
| c. | .16 | 50 | 95 | 100 | 100 | 30 | 90 | 40 | 100 | 70 | 100 | 100 | 100 | 100 | 90 | 100 | 70 | 0 | 0 | 60 |
| 2a. | 2.5 | 100 | — | 100 | — | — | 100 | 100 | 100 | 100 | 100 | 100 | 100 | 100 | 90 | 100 | 100 | 40 | 20 | 100 |
| b. | .63 | 50 | — | 50 | — | — | 100 | 100 | 100 | 100 | 100 | 100 | 100 | 100 | 50 | 100 | 100 | 0 | 0 | 100 |
| c. | .16 | 50 | — | 50 | — | — | 100 | 50 | 100 | 100 | 100 | 100 | 60 | 100 | 0 | 100 | 70 | 0 | 0 | 0 |
| 4a. | 2.5 | — | 100 | 100 | — | — | 100 | 100 | 100 | 100 | 100 | 100 | 100 | 100 | 90 | 100 | 100 | 50 | 70 | 100 |
| b. | .63 | — | 100 | 100 | — | — | 100 | 100 | 100 | 100 | 100 | 100 | 100 | 100 | 90 | 100 | 100 | 0 | 20 | 80 |
| c. | .16 | — | 50 | 70 | — | — | 100 | 100 | 100 | 90 | 100 | 100 | 90 | 70 | 0 | 100 | 60 | 0 | 0 | 60 |
| 5a. | 2.5 | — | — | — | — | — | 100 | 100 | 100 | 100 | 100 | — | 100 | 100 | 90 | 100 | — | 10 | 40 | 100 |
| b. | .63 | — | — | — | — | — | 50 | 100 | 80 | 100 | 100 | — | 100 | 100 | 70 | 100 | — | 0 | 0 | 80 |
| c. | .16 | — | — | — | — | — | 0 | 0 | 30 | 40 | 100 | — | 100 | 30 | 0 | 100 | — | 0 | 0 | 60 |
| 8a. | 2.5 | 0 | — | 90 | — | — | 100 | 100 | 100 | 100 | 100 | 50 | 100 | 100 | 0 | 100 | 50 | 0 | 0 | 20 |
| b. | .63 | 0 | — | 50 | — | — | 100 | 0 | 50 | 50 | 90 | 50 | 100 | 50 | 0 | 100 | 0 | 0 | 0 | 0 |
| c. | .16 | 0 | — | 0 | — | — | 50 | 0 | 0 | 0 | 50 | 0 | 20 | 0 | 0 | 0 | 0 | 0 | 0 | 0 |
| 10a. | 2.5 | — | — | — | — | — | 100 | 100 | 100 | 100 | 100 | — | 100 | 100 | 70 | 100 | — | 10 | 60 | 100 |
| b. | .16 | — | — | — | — | — | 100 | 100 | 100 | 100 | 100 | — | 100 | 20 | 0 | 100 | — | 0 | 0 | 20 |
| 11a. | 2.5 | — | 100 | 100 | 100 | 90 | 100 | — | — | 100 | 100 | 100 | — | — | — | — | — | 0 | 10 | 100 |
| b. | .16 | — | 100 | 100 | 40 | 0 | 40 | — | — | 100 | 100 | 100 | — | — | — | — | — | 0 | 0 | 20 |
| 12a. | 5.0 | 100 | 100 | 100 | 100 | 50 | 100 | 70 | 70 | — | 100 | 100 | — | — | — | — | — | 0 | 0 | 100 |
| b. | .63 | 90 | 90 | 100 | 100 | 30 | 100 | 60 | 40 | — | 100 | 0 | — | — | — | — | — | 0 | 0 | 40 |
| 21a. | 2.5 | 30 | — | 100 | — | — | 100 | 100 | 100 | 100 | 100 | 100 | 100 | 50 | 0 | 100 | 100 | 0 | 0 | 100 |
| b. | .16 | 0 | — | 10 | — | — | 0 | 50 | 100 | 100 | 100 | 0 | 100 | 0 | 0 | 0 | 0 | 0 | 0 | 0 |
| 22 | 1.25 | — | 40 | 0 | 0 | 0 | 10 | — | — | 20 | 100 | 0 | — | — | — | — | — | 0 | 0 | 80 |
| 34a. | 2.5 | 90 | — | 100 | — | — | 100 | 50 | 100 | 100 | 100 | 100 | 100 | 20 | 100 | 50 | 0 | 10 | 70 | |
| b. | .63 | 70 | — | 50 | — | — | 50 | 0 | 20 | 70 | 100 | 50 | 100 | 0 | 100 | 0 | 0 | 0 | 20 | |
| 35a. | 2.5 | 100 | 100 | 100 | 100 | 90 | 100 | 100 | 85 | 100 | 100 | 100 | — | — | — | — | — | 60 | 80 | 100 |

TABLE II-continued

| Cmpd. No. | Dosage lbs/Acre | Plant Species/% Control |||||||||||||||||
|---|---|---|---|---|---|---|---|---|---|---|---|---|---|---|---|---|---|---|
| | | Weeds ||||||||||| | | | | Crops ||||
| | | A | B | C | D | E | G | H | I | J | K | L | S | T | U | V | W | N | O | P |
| b. | .63 | 100 | 100 | 100 | 100 | 60 | 100 | 70 | 75 | 100 | 100 | 100 | — | — | — | — | — | 20 | 40 | 100 |
| c. | .16 | 90 | 90 | 60 | 90 | 60 | 60 | 40 | 40 | 50 | 100 | 50 | — | — | — | — | — | 0 | 0 | 40 |
| 36a. | 10.0 | 100 | — | 100 | — | — | 100 | 60 | 95 | 100 | 100 | 30 | 100 | 100 | 30 | 100 | 100 | 0 | 0 | 100 |
| b. | 2.5 | 80 | — | 50 | — | — | 0 | 40 | 30 | 100 | 100 | 30 | 0 | 50 | 0 | 100 | 20 | 0 | 0 | 50 |
| 37a. | 1.25 | — | 90 | 100 | 100 | 80 | 100 | — | — | 90 | 100 | 100 | — | — | — | — | — | 0 | 50 | 95 |
| b. | 0.16 | — | 0 | 0 | 90 | 0 | 100 | — | — | 0 | 50 | 0 | — | — | — | — | — | 0 | 0 | 10 |
| 38a. | 2.5 | — | 95 | 100 | 100 | 70 | 90 | — | — | 100 | 100 | 100 | — | — | — | — | — | 0 | 20 | 100 |
| b. | 0.63 | — | 20 | 60 | 100 | 20 | 50 | — | — | 50 | 95 | 50 | — | — | — | — | — | 0 | 0 | 20 |
| 39a. | 1.25 | — | 100 | 100 | 100 | 100 | 70 | — | — | 100 | 100 | 100 | — | — | — | — | — | 10 | 50 | 100 |
| b. | 0.32 | — | 100 | 40 | 50 | 100 | 30 | — | — | 80 | 100 | 100 | — | — | — | — | — | 0 | 20 | 80 |
| 40a. | 2.5 | — | 95 | 95 | 100 | 30 | 50 | — | — | 90 | 100 | 50 | — | — | — | — | — | 0 | 0 | 60 |
| b. | .63 | — | 0 | 80 | 100 | 10 | 0 | — | — | 20 | 50 | 0 | — | — | — | — | — | 0 | 0 | 0 |
| 41a. | 1.25 | — | 100 | 100 | 100 | 50 | 100 | — | — | 90 | 100 | 100 | — | — | — | — | — | 10 | 30 | 90 |
| b. | .32 | — | 90 | 40 | 90 | 0 | 50 | — | — | 50 | 90 | 60 | — | — | — | — | — | 0 | 0 | 20 |
| 42a. | 5.0 | — | 100 | 100 | 80 | 0 | 70 | — | — | 90 | 100 | 100 | — | — | — | — | — | 0 | 0 | 50 |
| b. | 1.25 | — | 80 | 90 | 0 | 0 | 40 | — | — | 60 | 100 | 0 | — | — | — | — | — | 0 | 0 | 10 |
| 43a. | 10.0 | — | 0 | 70 | 0 | 0 | 60 | — | — | 100 | 100 | 100 | — | — | — | — | — | 0 | 0 | 30 |
| b. | 0.63 | — | 0 | 0 | 0 | 0 | 0 | — | — | 0 | 100 | 0 | — | — | — | — | — | 0 | 0 | 0 |
| 44a. | 10.0 | — | 100 | 100 | 100 | 0 | 90 | — | — | 100 | 100 | 100 | — | — | — | — | — | 0 | 0 | 100 |
| b. | 1.25 | — | 95 | 90 | 0 | 0 | 50 | — | — | 100 | 70 | 70 | — | — | — | — | — | 0 | 0 | 100 |
| 45a. | 1.25 | — | 90 | 100 | 90 | 70 | 100 | — | — | 100 | 100 | 100 | — | — | — | — | — | 10 | 40 | 100 |
| b. | 0.32 | — | 90 | 100 | 90 | 50 | 90 | — | — | 100 | 100 | 50 | — | — | — | — | — | 0 | 0 | 100 |
| 46a. | 10.0 | — | 100 | 100 | 100 | 0 | 70 | — | — | 0 | 100 | 100 | — | — | — | — | — | 0 | 0 | 100 |
| b. | 2.5 | — | 70 | 80 | 90 | 0 | 100 | — | — | 0 | 100 | 50 | — | — | — | — | — | 0 | 0 | 80 |
| 47a. | 10.0 | 100 | 70 | 70 | 60 | 60 | 100 | 70 | 100 | 100 | 95 | 70 | — | — | — | — | — | 20 | 20 | 100 |
| b. | 1.25 | 70 | 40 | 50 | 50 | 10 | 80 | 40 | 80 | 80 | 100 | 0 | — | — | — | — | — | 0 | 0 | 70 |
| 48a. | 10.0 | 100 | 100 | 100 | 100 | 60 | 90 | 90 | 100 | 100 | 100 | 100 | — | — | — | — | — | 20 | 10 | 100 |
| b. | 1.25 | 95 | 95 | 60 | 70 | 20 | 50 | 20 | 60 | 80 | 100 | 70 | — | — | — | — | — | 0 | 0 | 60 |
| 49 | 5.0 | 70 | 50 | 40 | 70 | 0 | 80 | 10 | 50 | 90 | 90 | 10 | — | — | — | — | — | 0 | 0 | 40 |
| 50a. | 5.0 | 90 | 80 | 80 | 100 | 50 | 100 | 60 | 60 | 95 | 90 | 70 | — | — | — | — | — | 0 | 0 | 40 |
| b. | 0.63 | 60 | 50 | 20 | 80 | 20 | 100 | 40 | 0 | 20 | 100 | 0 | — | — | — | — | — | 0 | 0 | 0 |
| 51a. | 1.25 | — | 100 | 100 | 100 | 80 | 100 | — | — | 100 | 100 | 100 | — | — | — | — | — | 20 | 40 | 70 |
| b. | 0.32 | — | 40 | 80 | 100 | 30 | 50 | — | — | 40 | 100 | 50 | — | — | — | — | — | 0 | 0 | 20 |
| 52a. | 10.0 | 100 | — | 80 | 100 | 0 | 100 | 100 | 25 | 100 | — | — | — | — | — | — | — | — | 0 | 25 |
| b. | 0.63 | 55 | — | 0 | 30 | 0 | 100 | 90 | 0 | 45 | — | — | — | — | — | — | — | — | 0 | 0 |
| 53a. | 10.0 | 90 | — | 100 | 100 | 20 | 100 | 100 | 30 | 95 | — | — | — | — | — | — | — | — | 0 | 90 |
| b. | 1.25 | 30 | — | 90 | 70 | 0 | 100 | 100 | 0 | 100 | — | — | — | — | — | — | — | — | 0 | 30 |

In further operations, each of the N-(4-((6-chloro-2-pyridinyl)oxy)phenyl)propanamide, N-(3-chloro-4-((6-chloro-2-pyridinyl)oxy)phenyl)propanamide, N-(4-((6-chloro-2-pyridinyl)oxy)phenyl)acetamide and N-(4-((6-fluoro-2-pyridinyl)oxy)phenyl)acetamide compounds was found to give substantial to complete pre- and post-emergence control of crabgrass at a dosage rate about 10.0 pounds per acre.

In additional post-emergence operations, each of N'-((4-(5-cyano-2-pyridinyl)oxy)phenyl)-N,N-dimethyl urea (Compound 56) and N'-(4-((6-chloro-5-cyano-2-pyridinyl)oxy)phenyl)-N,N-dimethyl urea (Compound 57) was found to give complete control of species (A), (I) and (J) at a dosage rate of about 10.0 pounds per acre.

The foregoing data illustrate the general phytotoxic activity as well as selective phytotoxic activity of the compounds of the present invention. Although selective pre- and post- emergence activity has been demonstrated at several rates of application, it is to be understood that further specific selective operations and crop specificity are in many instances, obtainable by employing lower dosage rates than demonstrated above.

The substituted halopyridine, acetamidophenate, carbamoyl halide, nitro(thio)phenol, hydroxylamine, pyrrolidine and piperidine reactants employed in the present invention are either readily available or can be prepared according to procedures which are known or are analogous to those set forth in the open literature.

Although the invention is described with respect to specific embodiments and modifications, the details thereof are not to be construed as limitations except to the extent indicated in the following claims:

I claim:
1. A compound corresponding to the formula:

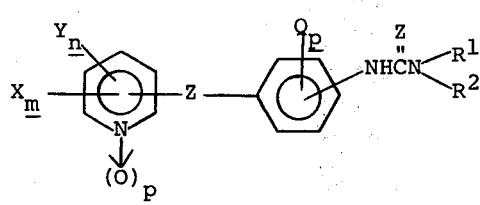

wherein:
each $p$ independently represents an integer of 0 or 1;
each X independently represents bromo, chloro, iodo or fluoro;
$m$ represents an integer of 0 to 4, inclusive;
each Y independently represents nitro, $ZR^3$, $-C(X')_3$ or

$n$ represents an integer of 0 to 2, inclusive;
each Z independently represents oxygen or sulfur;
Q represents methyl, ethyl, halo, nitro or trifluoromethyl;
each X' independently represents hydrogen or halo;
$R^1$ represents hydrogen, alkyl of from 1 to 4 carbon atoms or alkoxy of from 1 to 4 carbon atoms;
$R^2$ represents alkyl of from 1 to 3 carbon atoms or

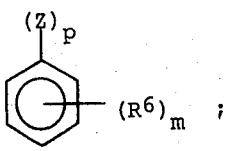

$R^3$ represents alkyl of from 1 to 3 carbon atoms;
$R^4$ and $R^5$ each independently represent hydrogen or alkyl of from 1 to 4 carbon atoms; and
each $R^6$ represents halo or alkyl of from 1 to 3 carbon atoms.

2. The compound of claim 1 wherein $n$ is 0 and $m$ is at least 1.

3. The compound of claim 1 wherein $m$ is 0 and $n$ is at least 1.

4. The compound of claim 1 wherein the sum of $n + m$ is one and X or Y is substituted on the 6-ring position.

5. The compound of claim 1 wherein $m$ is 1, $n$ is 0, X is substituted in the 6-ring position of the pyridine moiety.

6. The compound of claim 1 wherein $m$ is 0, $n$ is 1 and Y is substituted in the 6-ring position of the pyridine moiety.

7. The compound of claim 1 wherein $R^1$ and $R^2$ each represent alkyl.

8. The compound of claim 1 wherein $R^1$ is alkoxy and $R^2$ is alkyl.

9. The compound of claim 1 which is N'-(4-((6-(trifluoromethyl)-2-pyridinyl)oxy)phenyl)-N,N-dimethyl urea.

10. The compound of claim 1 which is N'-(4-((6-chloro-2-pyridinyl)oxy)phenyl)-N-methoxy-N-methyl urea.

11. The compound of claim 1 which is N'-(4-((6-chloro-2-pyridinyl)oxy)phenyl)-N,N-dimethyl urea.

12. The compound of claim 1 which is N'-(4-((6-chloro-2-pyridinyl)thio)phenyl)-N-methoxy-N-methyl urea.

13. The compound of claim 1 which is N-methoxy-N-methyl-N'-((6-trifluoromethyl)-2-pyridinyl)oxy)phenyl) urea.

14. The compound of claim 1 which is N'-(4-((6-bromo-2-pyridinyl)oxy)phenyl)-N,N-dimethyl urea.

* * * * *